(12) United States Patent
Daluge et al.

(10) Patent No.: US 6,552,193 B1
(45) Date of Patent: Apr. 22, 2003

(54) CHLOROPYRIMIDINE INTERMEDIATES

(75) Inventors: Susan Mary Daluge, Chapel Hill, NC (US); Michelle Joanne Fugett, Durham, NC (US); Michael Tolar Martin, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/419,416

(22) Filed: Oct. 15, 1999

Related U.S. Application Data

(60) Continuation of application No. 08/957,603, filed on Oct. 24, 1997, now Pat. No. 6,087,501, which is a division of application No. 08/682,743, filed as application No. PCT/GB95/00225 on Feb. 3, 1995, now Pat. No. 6,448,403.

(30) Foreign Application Priority Data

Feb. 4, 1994 (GB) .............................................. 9402161

(51) Int. Cl.[7] ........................................... C07D 239/48
(52) U.S. Cl. ...................................................... 544/332
(58) Field of Search .......................................... 544/332

(56) References Cited

U.S. PATENT DOCUMENTS 5,663,340 A * 9/1997 Stucky et al. ................ 544/330

* cited by examiner

*Primary Examiner*—Richard L. Raymond
(74) *Attorney, Agent, or Firm*—Amy H. Fix

(57) ABSTRACT

The present invention is directed to a compound of formula (III)

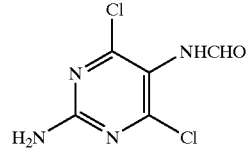

(III)

useful in the preparation of 9-substituted 2-aminopurines.

1 Claim, No Drawings

CHLOROPYRIMIDINE INTERMEDIATES

This is a continuation of Ser. No. 08/957,603, filed Oct. 24, 1997, now U.S. Pat. No. 6,087,501, which is a divisional of Ser. No. 08/682,743, filed Jul. 31, 1996, now U.S. Pat. No. 6,448,403, which is a §371 of PCT/GB95/00225, filed Feb. 3, 1995, which claims priority from GB 940216.5 filed Feb. 2, 1994.

The present invention relates to certain novel pyrimidine intermediates, processes for their preparation and their conversion to 9-substituted-2-aminopurines, such as certain carbocyclic, heterocyclic and acyclic purine nucleoside analogues, and salts, esters and pharmaceutically acceptable derivatives thereof.

A number of 2-aminopurine nucleoside analogues have been shown to be useful in the treatment or prophylaxis of viral infections, for example the compound of formula (A)

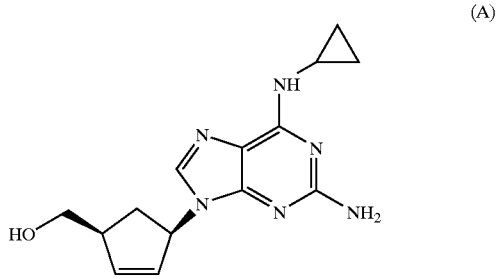

(A)

is described as having potent activity against human immunodeficiency virus (HIV) and hepatitis B virus (HBV) (EP 0434450).

Processes have been proposed for the preparation of 9-substituted-2-aminopurines, generally starting from a pyrimidine compound, coupling with a sugar analogue residue, and cyclisation to form the imidazole ring and introduction of any suitable 6-substituent.

Pyrimidine compounds which have been identified as being useful in the preparation of 9-substituted-2-aminopurines include 2,5-diamino-4,6-dichloropyrimidine, N,N'-(4,6-dichloro-2,5-pyrimidinediyl)bis formamide and also N-2-acylated pyrimidine derivatives such as the 2-acetamido and 2-isobutryamide derivatives (U.S. Pat. No. 5,087,697).

Processes for the synthesis of these intermediates generally involve a number of steps of which some are difficult to perform and produce poor yields, preventing any practical scale up of these processes above a few grams, and are thus difficult and uneconomical.

Process for the synthesis of the intermediate 2,5-diamino-4,6-dichloropyrimidine include the direct chlorination of readily available 2,5-diamino-4,6-dihydroxypyrimidine using phosphorus oxychloride. The original examination of this reaction was carried out by Temple et al. (J. Org. Chem. 1975, 40: 3141–3142). These workers concluded that the reaction was unsuccessful, apparently because of degradation of the pyrimidine ring system. Hanson (SmithKline Beecham, WO 91/01310, U.S. Pat. No. 5,216,161) subsequently described a process for the direct chlorination of 2,5-diamino-4,6-dihydroxypyrimidine by refluxing with phosphorus oxychloride in the presence of large molar excesses of quaternary ammonium chlorides or amine hydrochlorides. We have examined this process and have obtained, repeatedly, much lower yields (<10%) of crude 2,5-diamino-4,6-dichloropyrimidine than those specified in the SmithKline Beecham patent specification. The extensive decomposition of the 2,5-diamino-4,6-dihydroxypyrimidine to tars which coat the equipment, combined with the problems of dealing with the copious solids due to the insoluble amine salts, constitute significant drawbacks and make scale-up of such a process impractical. The modifications of Legraverend et al. (Synthesis 1990: 587–589), namely using acetonitrile as a solvent and adding phosphorus pentachloride to the phosphorous oxychloride and quaternary ammonium chloride, result, in our experience in the isolation of approximately 30% (after chromatographic purification) of 2,5-diamino-4,6-dichloropyrimidine on a 2–5 gram scale. Again, scale-up beyond a few grams is impractical due to the formation of tarry precipitates.

A recent Lonza A G patent specification (EP 0 552 758) suggests that higher yields (35–65%) may be obtained with phosphorus oxychloride chlorination when the 5-amino group of 2,5-diamino-4,6-dihydroxypyrimidine is protected with an alkoxycarbonyl protecting group. This modification is claimed to simplify the chlorination step in that the amines and phosphorus pentachloride, employed in the prior processes discussed above are not required. This creates a new problem, namely the need to remove the alkoxycarbonyl protecting groups in order to be able to convert the pyrimidine intermediates to purines. Indeed, the Lonza A G specification does not show that such 5-protected 2,5-diamino-4,6-dichloropyrimidines may be converted to purines in an advantageous manner.

A process for the synthesis of N,N'-(4,6-dichloro-2,5-pyrimidinediyl)bis formamide is the reaction of 2,5-diamino-4,6-dichloropyrimidine with formic acid and acetic anhydride (Harnden et al., J. Med. Chem. 1990, 33: 187–196 and U.S. Pat. No. 5,159,076).

The 5-step route to the N-2-acylated derivatives, and also to 2,5-diamino-4,6-dichloropyrimidine required for the synthesis of N,N'-(4,6-dichloro-2,5-pyrimidinediyl)bis-formamide (Temple et al., J. Org. Chem. 1975, 40: 3141–3142), starts from 2-amino-6-chloropyrimidin-4-one and contains steps, which include the introduction of the 5-nitro group and the subsequent handling and reduction of very reactive 5-nitro-4,6-dichloropyrimidine intermediates, which make scale-up impractical. The yields on a number of the steps to these intermediates are poor (Legraverend et al., Synthesis 1990: 587–589).

We have now discovered certain new pyrimidine intermediates which are useful in a new synthetic route for the preparation of the above 9-substituted-2-aminopurines and in addition which can be used in the synthesis of the known intermediates described above.

In one aspect of this invention we provide the following novel intermediates which may be utilised in the synthesis of 2-aminopurines, namely compounds of formulae (I), (II) and (III);

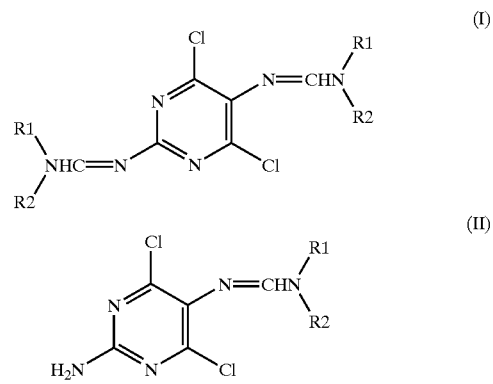

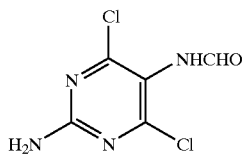
(III)

wherein $R^1$ and $R_2$, which can be the same or different, are selected from $C_{1-8}$ straight-chain alkyl, $C_{1-8}$ branched alkyl, $C_{3-8}$ cycloalkyl, and aryl groups (such as phenyl or naphthyl), which may be optionally substituted, for example by $C_{1-4}$ alkyl or halogen (e.g. Cl). In a preferred embodiment of the invention $R^1$ and $R^2$ are both methyl.

These novel intermediates can be readily prepared in good yields and are useful for the preparation of a wide variety of different types of 2-aminopurines including the nucleoside analogue of formula (A), famciclovir (EP 0182024), penciclovir (EP 0141927), H2G (EP 0343133), (1'S,3'S,4'S)-2-amino-1,9-dihydro-9-[3,4-dihydroxy-3-hydroxymethyl-1-cyclopentyl]-6H-purin-6-one (EP 0420518), and other 9-substituted-2-aminopurines provides that the 9-substituent is not attached by a glycosidic bond.

In a further aspect of this invention we provide processes for the synthesis of the novel intermediates of formulae (I), (II) and (III), and the known intermediates 2,5-diamino-4,6-dichloropyrimidine(IV). These processes are illustrated in the simplified diagram below which is designed for illustration only of the possible ways of synthesising these intermediates;

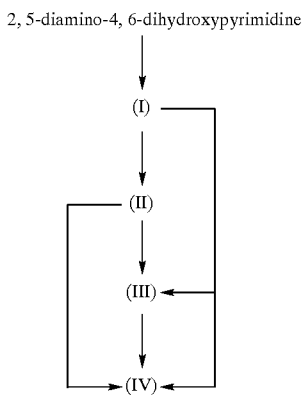

The present invention also provides a process for the preparation of compounds of formula (I) which comprises chlorination of 2,5-diamino-4,6-dihydroxypyrimidine with a halomethylenimminium salt (Vilsmeier reagent) of formula (V).

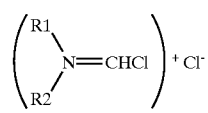
(V)

wherein $R^1$ and $R^2$ are as defined above.

Compounds of formula (V), may be prepared from a variety of formamides of secondary amines by reaction with a variety of acid halides, such as phosphorus oxychloride, phosphorus pentachloride, thionyl chloride, phosgene, and oxalyl chloride, for example as detailed in a review by C. M. Marson, Tetrahedron, 1992, 48: 3660–3720 and references therein.

The advantages of protecting the diaminopyrimidine from extensive decomposition during chlorination is achieved by the in situ protection of the amino groups with two molar equivalents of Vilsmeier reagent (V) to give a bis-formamide intermediate (detected by thin-layer chromatography), which is subsequently chlorinated to a compound of formula (I) as the reaction with additional equivalents of Vilsmeier reagent proceeds. The improved solubility of such bis-formamidine derivatives is an added advantage of this process, facilitating the subsequent chlorination to compounds of formula (I) and their isolation and simple purification.

The disadvantage of the use of 5-alkoxycarbonyl protecting groups, as described in the Lonza specification (EP 0552758) is avoided since the formamidine groups in compounds of formula (I) are readily hydrolysed under mild conditions in a step-wise manner to form the intermediates (II) and (III); or alternatively compounds of formula (I) can be directly hydrolysed to compounds of formula (III).

The compound 2,5-diamino-4,6-dichloropyrimidine (IV) can be prepared by:

A) the hydrolysis of a compound of formula (I);
B) the hydrolysis of a compound of formula (II); or
C) the hydrolysis of a compound of formula (III).

The hydrolysis of (I), (II), or (III) to 2,5-diamino-4,6-dichloropyrimidine is conveniently carried out at pH 3±0.5 by adding a water-miscible cosolvent, such as ethanol. The hydrolysis is more efficient at pH 1–2, with shorter reaction times required than at a higher pH. It is advisable at pH 1–2, however, to protect 2,5-diamino-4,6-dichloropyrimidine from hydrolysis to hydroxypyrimidines by extraction, as it is formed, into an organic layer which is not miscible with the aqueous acid. When the pH of the aqueous layer is below 1, extraction of the product into the organic layer is inefficient (the $pK_a$ of (IV) was found to be ca 0.5 and the pyrimidine ring is thus significantly protonated below pH 1). Preferably, the acid used for this hydrolysis should be one which is not appreciably soluble in the organic layer, e.g. phosphoric or sulfuric acid. The organic solvent should be one which is stable to aqueous acid and in which (IV) is soluble. Satisfactory solvents for the organic layer include toluene and halocarbon solvents such as methylene chloride, chloroform, and 1,2-dichloroethane. At completion, the organic layer is simply washed, e.g. with saturated aqueous bicarbonate, dried and concentrated to provide (IV) with no purification required.

Compounds of formula (III) can be prepared by:

A) selective hydrolysis of a compound of formula (I); or
B) selective hydrolysis of a compound of formula (II).

The hydrolysis of compounds of formula (I) or (II) or (III) is most efficiently carried out in dilute aqueous acid, preferably in dilute aqueous mineral acid such as sulfuric acid, hydrochloric acid, or phosphoric acid. Prolonged exposure to pH below 1 should be avoided as the chloropyrimidine ring is protonated significantly below pH 1 and may therefore undergo attack by water, generating undesired hydroxypyrimidine by-products. Preferably, the pH is maintained above 2 and optimally at 3±0.5 for the efficient formation of (III). In this optimal pH range, the formamidine groups of (I) and (II) are selectively hydrolysed to give (III) in approximately 70% yield. As the hydrolysis of the formamidine groups of (I) and (II) proceed, the secondary amine from which the Vilsmeier reagent (V) was formed (HNR$^1$R$^2$) is liberated and causes the pH of the solution to rise, thus slowing the hydrolyses. In addition, with certain reaction aliphatic amines HNR$^1$R$^2$, such as N,N-dimethylamine, it is necessary to maintain a pH sufficiently low to prevent the chloro groups of the pyrimidine ring from displacement by the secondary amine. We have found that maintaining the pH of the reaction mixtures below 4 avoids significant displacement of the chloro groups by the secondary amine, even with amines as reactive as N,N-dimethylamine. It was thus found optimal to buffer the hydrolyses of (I) and (II) to (III) at pH 3±0.5 or to add increments of acid throughout the hydrolyses in order to maintain the pH in this range.

Optimally, the hydrolysis of compounds of formula (I) or (II) to (III) is carried out in a minimum of water with the pH controlled as described above. Under these conditions, (III) precipitates as formed and is simply filtered off and washed with water. The hydrolysis is carried out at gentle reflux for 4 hours, or at lower temperatures for longer periods of time.

The compounds of formula (II) can be prepared by the selective hydrolysis of the compounds of formula (I). Preferably the selective hydrolysis is carried out with slightly more than two molar equivalents of mineral acid in water or ethanol and warmed for 15–30 minutes.

The compounds of formula (I) can be prepared by reacting 2,5-diamino-4,6-dihydroxypyrimidine with a Vilsmeier reagent of formula (V).

The compound 2,5-diamino-4,6-dihydroxypyrimidine is commercially available (Sigma, Maybridge BTB, Pfaltz and Bauer, Polyorganix).

The novel bis-formamidines of formula (I) are formed and isolated conveniently in high yield when the 2,5-diamino-4,6-dihydroxypyrimidine (or a salt thereof, such as the hydrochloride or the hemisulfate) is treated with at least 4 molar equivalents of a Vilsmeier reagent (V). These chlorination reactions proceed under extremely mild conditions without the formation of copious tarry precipitates which characterises direct chlorinations, as previously described with phosphorus oxychloride and phosphorus oxychloride/quaternary ammonium halides. The Vilsmeier chlorination of 2,5-diamino-4,6-dihydroxypyrimidine may be carried out in an inert solvent, such as toluene, chloroalkenes, or chloroalkanes (such as methylene chloride, chloroform or 1,2-dichloroethane). Preferably the solvent is 1,2-dichloroethane, chloroform, or methylene chloride. The chlorination may be carried out at 0 to 110° C., preferably at 40–100° C., conveniently at reflux for the solvent used. Reaction times are typically 12 to 48 hours. Isolation of compounds of formula (I) is simple and can be readily scaled-up, involving simply washing the reaction solution with an aqueous solution containing sufficient base, such as sodium bicarbonate, to neutralize any hydrogen chloride formed and then concentrating the dried organic layer to obtain the novel chlorinated pyrimidines of formula (I). The compounds of formula (I) are generally stable and may be precipitated from a variety of solvents, such as ethyl acetate, and stored or used without further purification.

Particularly preferred examples of the compounds of formulae (I), (II) and (III) are:

a) 4,6-Dichloro-2,5-bis-[(dimethylamino)methyleneamino]pyrimidine b) 2-Amino-4,6-dichloro-6-[(dimethylamino)methyleneamino]pyrimidine c) N-(2-Amino-4,6-dichloro-5-pyrimidinyl)formamide According to a further aspect of this invention the novel intermediate of formula (III) can be used in the synthesis of 2-amino-6-chloropurines. In addition compounds of formula (I) or (II) may also be used in the synthesis of 2-amino-6-chloropurines nucleosides, provides that the amine $HNR^1R^2$ (where $R^1$ and $R^2$ are defined earlier) liberated, during the conversion of the pyrimidine intermediate to the purine, is sufficiently unreactive towards the displacement of the chloro group of the 2-amino-6-chloropurines generated The compounds of formula (III) share with the previously described N-2-acylated derivatives the property of greater reactivity than 2,5-diamino-4,6-dichloropyrimidine toward displacement of a chloro group by an appropriate primary amine or protected hydroxylamine. However, such condensations with (III) (described in more detail below) may be carried out under milder conditions at lower temperatures and with shorter reaction times than with compound (IV), thus resulting in less decomposition of the amines. The condensation products (VI) are isolated in greater yield and purity than the corresponding products (VIII) formed in condensations with 2,5-diamino-4,6-dichloropyrimidine (IV). Another advantage of the use of the intermediate (III) over the previously described N-2-acylated derivatives, in addition to greater ease of synthesis, is that the purines generated from (III) do not require deprotection, i.e. hydrolysis of the N-2-acyl group (these longer processes are described in U.S. Pat. Nos. 5,087,697 and 5,159,076).

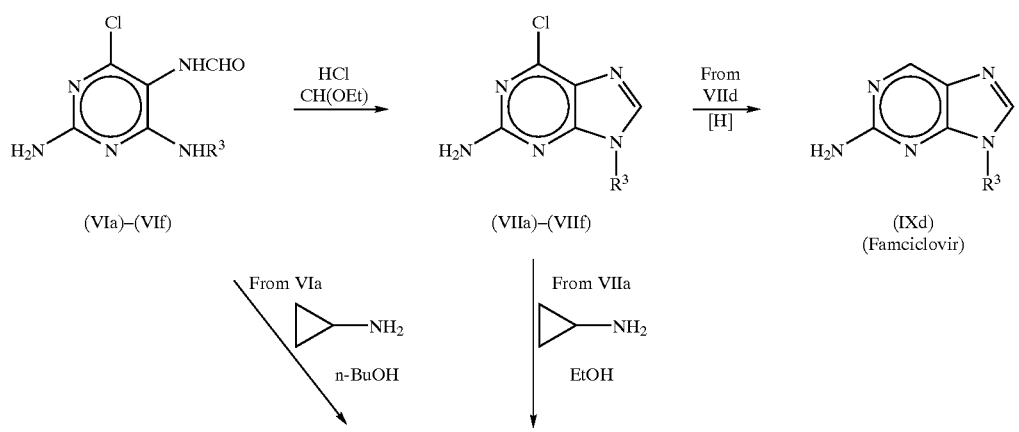

-continued

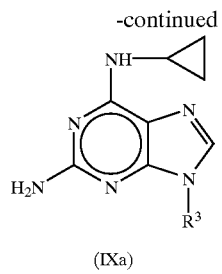

(IXa)

Wherein R³ is hereinafter defined.

The compound of formula (III) can be used to prepare the novel intermediates of formula (VI) which represent a further feature of the invention:

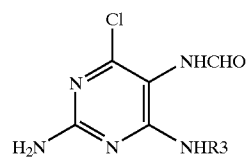
(VI)

wherein R³ may be hydrogen or any group which is not attached by a glycosidic bond.

Preferably R³ is a hydroxyl or a protected hydroxyl; or a carbocyclic group (e.g. C$_{3-7}$ carbocyclic), an acyclic group (e.g. C$_{2-8}$ hydrocarbyl) wherein carbon atoms may be substituted by one or more heteroatoms such as N, O or S, or a heterocyclic group (e.g. C$_{4-7}$ heterocyclic) in which at least one carbon atom is replaced by a N, O, or S atom, or a substituted analogue of any thereof (e.g. such substituents are independently selected from C$_{1-4}$ alkyl, C$_{1-4}$ alkoxy, hydroxyl or protected hydroxyl, azido, phosphonyl, or halogen), provided that such groups are not attached by a glycosidic bond.

Preferred groups for R³ are hydroxyl or protected hydroxyl.

Further preferred groups for R³ are a.

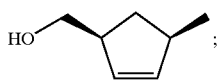;

b.

H;

c.

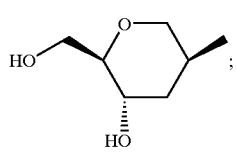;

d.

(AcOCH$_2$)$_2$CHCH$_2$CH$_2$—;

e.

HOCH$_2$CH$_2$CHCH$_2$—;
  |
  CH$_2$OH f.

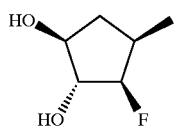

g.

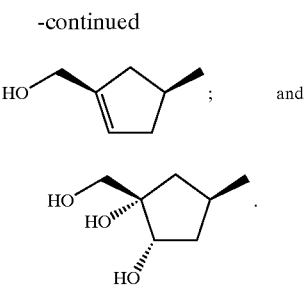; and h.

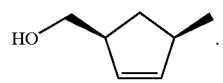.

A further preferred group for R³ is;

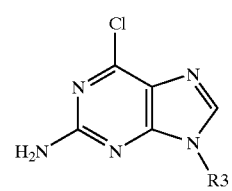.

Suitable groups for R³ are selected from a; b; c; d; e; and f, as defined above.

By "hydrocarbyl" it is meant a group containing only hydrogen and carbon atoms, which may contain double and/or triple bonds and which may be straight, branched, cyclic or aromatic.

According to a further feature of the invention we provide a process for the preparation of compounds of formula (VI) which comprises reacting a compound of formula (III) with an amine of formula R³NH$_2$, where R³ is defined above. Such condensations are preferably carried out at reflux in a solvent such as ethanol, butanol, water or acetonitrile in the presence of at least one equivalent of a base, such as trialkylamine or potassium or sodium carbonate.

Subsequent references to compounds of formula (VIa, b, c, d, e, f, g, or h) denote a compound of formula (VI) in which R³ is a group of a, b, c, d, e, f, g, or h as defined above.

A particularly preferred compound of formula (VI) is (1S,4R)-4-[(2-amino-6-chloro-5-formamido-4-pyrimidinyl)amino]-2-cyclopentene-1-methanol (VIa)

The novel intermediates (VI) can be converted by ring closure to the corresponding compounds of formula (VII):

(VII)

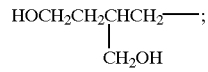

wherein R³ is defined above.

Ring closure of (VI) to (VII) is conveniently carried out in trialkylorthoformates (e.g. triethylorthoformate or trimethylorthoformate) with concentrated aqueous acid (e.g. 2–4 molar equivalents of hydrochloric, sulfuric acid or methane sulfonic). For example, the hydrochloride salt of (VIIa) i.e. wherein R³ represents group a, begins to precipitate from such orthoformate solutions of (VIa) within minutes and yields above 90% may be achieved by filtration of the precipitate, optimally after several hours at ambient temperature.

The synthesis of 9-substituted-2-amino-6-chloropurines, such as compounds of formula (VII), in this manner represents a significant improvement over previously published syntheses utilizing triaminopyrimidine intermediates such as (VIII):

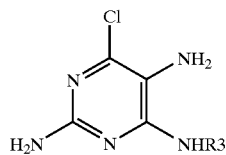
(VIII)

as described U.S. Pat. No. 4,916,224. The previously-described routes to intermediates such as (VIII) are longer and, more importantly, the number of steps to the purine targets after incorporation of the group R³ is greater. Also, triaminopyrimidine intermediates such as (VIII) are air- and light-sensitive and extremely difficult to purify due to their polarity and metal-chelating abilities (the isolation from the zinc reduction of diazo intermediates is especially problematic). The novel 5-formamido intermediates of formula (VI) are easily and directly attainable from compounds of formula (III) in one step and are generally solids which are stable and easily-purified by precipitation from a suitable solvent.

(1'S,3'S,4'S)-2-Amino-1,9-dihydro-9-[3,4-dihydroxy-3-hydroxymethyl-1-cyclopentyl]-6H-purin-6-one (IXh) (EP0420,518) may be prepared by condensation of the compounds of formula(III) with 4-amino-3-cyclopentene-1-methanol (U.S. Pat. No. 5,049,671) to form the compound of formula (VIg) followed by ring closure of the compound of formula (VIg) to prepare the compound of formula (VIIg), which may be hydroxylated, with osmium tetroxide/N-methyl-morpholine N-oxide to provide the compound of formula (VIIh). The compound of formula (VIIh) is hydrolysed to form the compound of formula (IXh).

2-Amino-6-chloropurine (VIIb) may be prepared by ring closure of novel 2,4-diamino-6-chloro-6-formamidopyrimidine (VIb), conveniently synthesized by condensation of the compound of formula (III) with ammonia. The compound of formula (VIIb) is an intermediate suitable for the synthesis of acyclic antiviral nucleosides, such as famciclovir wherein the 2-amino-6-chloropurine intermediate (VIId) is conveniently subjected to hydrogenolysis to the 2-aminopurine nucleoside.

Carbocyclic nucleosides may also be synthesized from the compound of formula (VIIb), for example by (Pd-catalyzed coupling with an appropriate carbocyclic intermediate as described in Mac Keith et al., J.Chem.Soc.Perkin Trans 1. 1993: 313–314 and references therein.

The compounds of formula (VIIa), (VIIc), (VIIe), (VIIf), (VIIg) and (VIIh) are conveniently hydrolyzed to the corresponding guanine compound by refluxing with aqueous base or acid.

As a further feature of this invention we have found an alternative process for the synthesis of 2,6-diaminopurines (wherein the 6-amino group is substituted by R⁴ and R⁵, which may be the same or different, and are selected from H, $C_{1-8}$alkyl, $C_{3-6}$cycloalkyl, aryl (such as phenyl), in particular R⁴ is H and R⁵ is cyclopropyl) directly from (VI) which advantageously eliminates a step in the process. Such 2-aminopurine compounds can be synthesised directly from the intermediates (VI) by refluxing the compound of formula (VI) with an excess of the amine (HNR⁴R⁵) in a refluxing solvent, such as ethanol, isopropanol, n-propanol, t-butanol or n-butanol.

In particular cases, it may be more useful to utilize 2,5-diamino-4,6-dichloropyrimidine(IV) to prepare compounds of formula (VIII), useful in the synthesis of 8-modified 2-aminopurine nucleoside analogues, such as 8-aza-2-aminopurines (which have broad-spectrum anti-herpes activities described in Storer et al., Spec. Publ. Roy. Soc. Chem (Rec. Adv. Chem. Anti-Infect. Agents) 1993, 119: 251–265); in such cases the intermediates (I), (II) and (III) can be used to provide (IV).

Pharmaceutically acceptable esters of certain compounds of the invention may be prepared by esterification using conventional methods known in the art. Such methods include, for example, the use of an appropriate acid halide or anhydride.

The compounds of the invention, including esters thereof, may be converted into pharmaceutically acceptable salts in a conventional manner by treatment with an appropriate acid or base. An ester or salt of a compound of the invention may be converted into the parent compound, for example, by hydrolysis.

The following examples are intended for illustration only and are not intended to limit the scope of the invention in any way.

EXAMPLE 1

4,6-Dichloro-2,5-bis-{[(dimethylamino)methylene]amino}pyrimidine 2,5-Diamino-4,6-dihydroxypyrimidine hemisulfate (Sigma, 25.0 g, 0.131 mole) was stirred in chloroform (A. R. Mallinckrodt, 400 mL) in a 2 L- 3-necked round bottom flask equipped with a reflux condenser (with source of nitrogen connected to the top of the condenser) and an exit for HCl gas connecting another neck of the flask to a NaOH trap. (Chloromethylene)dimethyl ammonium chloride (Vilsmeier reagent, Aldrich, 88.0 g, 0.651 mole as 95%) was washed into the flask with additional chloroform (400 mL). The reaction mixture was brought cautiously to reflux with nitrogen sweeping the HCl evolved into the trap. When the evolution of HCl slowed after about 1 hour of reflux, the sweep was stopped and the reaction kept under a gentle positive pressure of nitrogen from that point. Additional Vilsmeier reagent (50.0 g, 0.370 mole) was added after 24 hours and reflux continued for an additional 20 hours. The stirred reaction mixture (yellow solution with dark yellow solid) was cooled (ice bath) and diluted with water (sufficient to dissolve the solid, ca. 300 mL). The aqueous layer was adjusted to pH 7 with sodium hydroxide or solid sodium carbonate. The chloroform layer was separated, washed with water (3×400 mL), dried (sodium sulfate), and concentrated in vacuo to a dark yellow solid (36 g). This solid was dissolved in ethyl acetate (300 mL), stirred with charcoal (1 g), and filtered with a silica gel pad (3×3 in., packed in ethyl acetate). The pad was washed with additional ethyl acetate and eluents concentrated in vacuo to leave the title compound as a light tan solid (30.75 g, 81%); m.p. 116–119° C.; 1H-NMR identical to that of recrystallized samples.

Anal. Calcd. for $C_{10}H_{14}N_6Cl_2$. 0.10 EtOAc: C, 41.92; H, 5.01; N, 28.20; Cl, 23.80. Found: C, 42.23; H, 4.95; N, 28.46; Cl, 24.11.

Recrystallization of such as sample from ethyl acetate gave the title compound as white granules; m.p. 123–125° C.; mass spectrum (CI/CH₄): 291, 289 (M+1); ¹H-NMR (DMSO-$d_6$)δ: 8.49 and 8.69 (both s, 1 each, 2CH), 3.16 (s, 3, CH₃), 3.03 (s, 6, 2CH₃), 2.97 (s, 3, Ch₃); UV (pH 7 phosphate buffer) λmax 296 nM (ε33,300), λmin 248 (5200).

Anal. Calcd. for C10H14N6Cl2: C, 41.54; H, 4.88; N, 29.06; Cl, 24.52. Found: C, 41.59; H, 4.91; N, 29.01; Cl, 24.47.

EXAMPLE 2

2-Amino-4,6-dichloro-5-{[(dimethylamino)methylene]amino}pyrimidine 4,6-Dichloro-2,5-bis-{[(dimethylamino)methylene]amino}pyrimidine (Example 1, 5.87 g, 20.3 mmol) was dissolved in 95% ethanol (200 mL) and 6 N aqueous hydrochloric acid (13.5 mL) added. The solution was heated in an oil bath at 55° C. under nitrogen for 30 minutes, at which point TLC (silica gel, 5% methanol-chloroform) showed that starting material had been cleanly converted to a lower-Rf product. The cooled (ice bath) solution was adjusted to pH ~8 with concentrated ammonium hydroxide and the resulting mixture (white precipitate formed) concentrated on a rotary evaporator to ~5 mL to remove ethanol. Additional water (20 mL) was added and the cooled mixture was filtered. The white precipitate was washed with additional water (2×20 mL) and dried to give the title compound as a white powder (4.50 g, 95%), m.p. >dec 250° C.; mass spectrum (CI/CH4): 236, 234 (M+1); $^1$H-NMR (DMSO-d6) δ: 7.59 (s, 1, CH), 6.90 (s, 2, NH2), 3.00 and 2.94 (both s, 3 each, 2CH3); UV (pH 7 phosphate buffer) λmax: 328 nM (ε4500), 255 (15,800).

Anal. Calcd. for C7H9N5Cl2: C, 35.92; H, 3.88; N, 29.92; Cl, 30.29. Found: C, 35.66; H, 3.86; N, 29.74; Cl, 30.54.

In another experiment, 2,5-diamino-4,6-dihydroxypyrimidine hemisulfate (Sigma, 48.0 g, 0.250 mole) was reacted as in Example 1 with less Vilsmeier reagent (7.2 molar equivalents) and the resulting 4,6-dichloro-2,5-bis-{[(dimethylamino)methylene]amino}pyrimidine (92%), without recrystallization, was hydrolyzed in 95% ethanol (1 L) and 6 N aqueous hydrochloric acid (110 mL) to provide the title compound of the same purity (elemental analysis and 1H-NMR) as the characterized sample described above (44.2 g. 76% overall from 2,5-diamino-4,6-dihydroxypyrimidine hemisulfate).

EXAMPLE 3

N-(2-Amino-4,6-dichloro-5-pyrimidinyl)formamide (III)

A slurry of 2-amino-4,6-dichloro-5-{[(dimethylamino)methylene]amino}pyrimidine (Example 2, 1.50 g, 6.41 mmol) and 1.5 M aqueous potassium phosphate buffer (35 mL, prepared by adjusting the pH of a 1.5 M solution of KH2PO4 to 3.2 by addition of 85% phosphoric acid) was gently refluxed (in an oil bath at 125° C.). After 4 hours of reflux, the pH of the mixture was adjusted from 4 to 3 by addition of 4 drops of 85% phosphoric acid. After a total of 6 hours of reflux, TLC(silica gel plates developed in 5% methanol-chloroform) showed that the starting material had been largely converted to a lower-Rf product. The solid was filtered and washed with water (5 mL), methanol (5 mL), and dried to give the title compound as a white solid (0.900 g, 68%), m.p.>250° C. dec.; mass spectrum (CI/CH4): 209, 207 (M+1); 1H-NMR (DMSO-d6)δ: 9.81 and 9.46 (s and d, J=11 Hz, total 1, NH), 8.25 and 8.00 (s and d, J=11 Hz, total 1, CHO), 7.69 and 7.63 (both s, total 2, NH2).

Anal. Calcd for C5H4N4OCl2: C, 29.01; H, 1.95; N, 27.07; Cl, 34.25. Found: C, 29.12; H, 1.96; N, 27.13; Cl, 34.34.

In another experiment, a slurry of 2-amino-4,6-dichloro-5-{[(dimethylamino)methylene]amino}-pyrimidine (Example 2, 25.0 g, 0.107 mol) in 1.5 M aqueous potassium phosphate buffer (300 mL, prepared as above) was gently refluxed for 4 hours. pH was maintained at 3.2 by addition of 85% phosphoric acid, as required, throughout this period. The precipitate was filtered, washed with water (3×10 mL), methanol (2×10 mL), and dried (50° C., 25 mm Hg) to give the title compound as an off-white powder (16.0 g, 72%) with purity identical to that of the characterized sample described above (elemental analysis and 1H-NMR).

EXAMPLE 4

2,5-Diamino-4,6-dichloropyrimidine (IV)

4,6-Dichloro-2,5-bis-{[(dimethylamino)methylene]amino}pyrimidine (Example 1, 1.00 g, 3.36 mmol) in ethanol (25 mL) and pH 3.2 aqueous potassium phosphate buffer (1.5 M, 10 mL, prepared as described in Example 3) was refluxed for 24 hours. During reflux, the pH was maintained at ca. 3 by addition of 85% phosphoric acid, as required. The ethanol was evaporated in vacuo and water added (10 mL). This solution was extracted with chloroform (3×25 mL). The combined chloroform layers were dried (sodium sulfate) and chloroform evaporated to leave a solid (0.40 g). Crystallization of this solid from ethanol-water/4:1 gave the title compound (IV) as off-white needles (0.324 g, 52%); darkens are shrinks to black solid above 185° C., does not become fluid below 300° C.; .[Lit. 198° C. (Legraverend et al., Synthesis 1990: 587–589) and 188–191° C. (Temple et al., J. Org. Chem. 1975, 40: 3141–3142)]; mass spectrum (CI/CH4): 181, 179 (M+1); 1H-NMR (DMSO-d6)δ: 6.50 (br s, 2, NH2), 4.73 (br s, 2, NH2).

Anal. Calcd. for C4H4N4Cl2.0.12 EtOH: C, 27.60; H, 2.58; N, 30.36; Cl, 38.42. Found: C, 27.99; H, 2.39; N, 30.42; Cl, 38.74.

EXAMPLE 5

2,5-Diamino-4,6-dichloropyrimidine (IV)

A mixture of 2-amino-4,6-dichloro-5-[(dimethylamino)methylene]amino}pyrimidine (Example 2, 500 mg, 2.14 mmol), pH 3.2 aqueous potassium phosphate buffer (1.5 M, 6 mL, prepared as described in Example 3), water (1 mL), and ethanol (5 mL) was refluxed gently for 28 hours. During the reflux period, pH was maintained at ca. 3 by addition of 85% phosphoric acid. Volatiles were evaporated in vacuo and the residual solids partitioned between water (30 mL, adjusted to pH 8 with dilute ammonium hydroxide) and chloroform (75 mL. The chloroform layer was dried (sodium sulfate) and the chloroform evaporated to leave off-white solid (0.30 g). Crystallization of this solid from ethanol:water/4:1 gave the title compound (IV) as light pink needles (332 mg, 61%); darkens and shrinks to black solid above 185° C., does not become fluid below 300° C.; 1H-NMR (DMSO-d6) and mass spectra identical to those described in Example 4.

Anal. Calcd. for C4H4N4Cl2: C, 26.83; H, 2.25; N, 31.30; Cl, 39.61. Found: C, 26.93; H, 2.25; N, 31.24; Cl, 39.52.

EXAMPLE 6

2,5-Diamino-4,6-dichloropyrimidine (IV)

N-(2-Amino-4,6-dichloro-5-pyrimidinyl)formamide (Example 3, 500 mg. 2.42 mmol) was dissolved in 0.1 N hydrochloric acid (5 mL, 2.5 mequiv) and ethanol (7 mL) at reflux. The solution was refluxed for 5 hours. Volatiles were removed in vacuo. The residue was partitioned between water (30 mL) adjusted to pH 8 with dilute ammonium hydroxide and ethyl acetate (75 mL). The ethyl acetate layer was dried (sodium sulfate). Evaporation of the ethyl acetate

13 left pink solid (0.40 g). Recrystallization of the solid from 95% ethanol gave the title compound (IV) as light pink needles (280 mg, 65%); darkens and shrinks to black solid above 185° C., does not become fluid below 300° C.; 1H-NMR (DMSO-d6) and mass spectra identical to those described in Example 4.

Anal. Calcd. for $C_4H_4N_4Cl_2$: C.26.83; H.2.25; N.31.30; Cl.39.61. Found C.26.95; H.2.24; N. 31.19; Cl. 39.53.

EXAMPLE 7

(1S,4R)-4-[(2-Amino-6-chloro-5-formamido-4-pyrimidinyl)amino]-2-cyclopentene-1-methanol (VIa)

N-(2-Amino-4,6-dichloro-5-pyrimidinyl)formamide (Example 3, 2.07 g, 10.0 mmol) was stirred in refluxing absolute ethanol (40 mL) under nitrogen to achieve partial dissolution. To this stirred mixture was added a solution of freshly prepared (1S,4R)-4-amino-2-cyclopentene-1-methanol (PCT Application 9204015.3, 1.57 g, 12.5 mmol as 90%) in ethanol (15 mL) followed by triethylamine (3.5 mL, 25 mmol, freshly distilled from calcium hydride). After 14 hours of reflux, the resulting dark solution was cooled and 1 N sodium hydroxide (10 mL) was added. The volatiles were evaporated in vacuo. The residual tan solid foam was dissolved in 5% methanol-ethyl acetate, and the solution was washed through a silica gel pad to give the title compound as an off-white solid (2.50 g, 88%), after evaporation of solvents. Recrystallization of the solid from ethyl acetate-methanol (20:1) gave the title compound (VIa) as fine white crystals (2.29 g, 81%), m.p. 177–178° C.; mass spectrum (CI/CH4): 286, 284 (M+1), 190, 188 (B+H); 1H-NMR (DMSO-d6)δ: 8.99 and 8.58 (s and d, J=11.1 Hz, total 1, amide NH), 8.11 and 7.80 (s and d, J=11.1 Hz, total 1, amide CH), 6.77 and 6.61 (two d, J=8.0 Hz) overlapping 6.60 and 6.48 (two br s, total 3, NH and NH2), 5.85 and 5.70 (two m, 1 each, CH=CH), 5.15–5.00 (m, 1, NCH), 4.71 (t, J=5.1, 1, OH), 3.45–3.30 (m overlapping H2O, OCH2), 2.80–2.65 (m, 1, CH), 2.45–2.25 and 1.45–1.30 (both m, 1 each, CH2); $[\alpha]^{20}_{589}$+21.2°, $[\alpha]^{20}_{578}$+22.2°, $[\alpha]^{20}_{546}$+25.2°, $[\alpha]^{20}_{436}$+41.4°, $[\alpha]^{20}_{365}$+48.3° (c 0.50, methanol).

Anal. Calcd. for $C_{11}H_{14}N_5O_2Cl$: C, 46.57; H, 4.97; N, 24.69; Cl, 12.50. Found: C, 46.63; H, 4.99; N, 24.58; Cl, 12.59.

EXAMPLE 8

(1S,4R)-4-(2-Amino-6-chloro-9-H-purin-9-yl)-2-cyclopentene-1-methanol Hydrochloride (VIIa)

A mixture of (1S,4R)-4-[(2-amino-6-chloro-5-formamido-4-pyrimidinyl)amino]-2-cyclopentene-1-methanol (Example 7, 1.00 g, 3.50 mmol) and triethylorthoformate (Aldrich, Sure Seal, 18 mL) was stirred while concentrated hydrochloric acid (37%, 1.25 mL) was added in one portion. The resulting clear, colorless solution was stirred under nitrogen. A white precipitate began to form after 15 minutes. After 4 hours, TLC of a drop of the reaction mixture dissolved in methanol and neutralized with sodium hydroxide (silica gel plates developed in 10% methanol-chloroform, visualized in UV light) showed almost complete conversion of VIa to a higher-Rf material. The precipitate was filtered, washed with t-butyl methyl ether (15 mL) and dried at 0.2 mm Hg/25° C. for 18 hours to give the title compound as a white powder (975 mg, 92%), m.p.>300° C. dec.; mass spectrum (CI/CH4): 266(M+1); 1H-NMR (DMSO-d6)δ: 8.18 (s, 1, purine CH), 7.2–6.7 (br s, NH2, OH overlapped by water), 6.20 and 5.90 (both m, 1 each, CH=CH), 5.48 (m, 1, NCH), 3.47 (d, J=5.7 Hz, 2, CH2O), 2.90 (m, 1, CH), 2.75–2.55 and 1.75–1.60 (both m, 1 each, CH2).

Anal. Calcd. for $C_{11}H_{12}N_5OCl.HCl$: C, 43.73; H, 4.34; N, 23.18; Cl, 23.48. Found: C, 43.62; H, 4.34; N, 23.07; Cl, 23.53.

EXAMPLE 9

(1S,4R)-4-[2-Amino-6-(cyclopropylamino)-9H-purin-9-yl]-2-cyclopentene-1-methanol (IXa)

A solution of (1S,4R)-4-chloro-5-formamido-6-{[(4-hydroxymethyl)-2-cyclopenten-1-yl]amino}pyrimidine (Example 8, 250 mg, 0.883 mmole) was refluxed gently (in an oil bath maintained at 130° C.) in n-butanol (dried over 4 A molecular sieves, 5 mL) under nitrogen with cyclopropylamine (Aldrich, 0.30 mL, 4.4 mmol) for 16 hours. A second portion of cyclopropylamine (0.15 mL) was added and reflux continued for an additional 5 hours. The volatiles were removed and the residual oil redissolved in ethanol-water (1:1) with 1 N sodium hydroxide (0.5 mL). Volatiles were again removed and the residue chromatographed on a silica gel flash column (1×10"). (1S,4R)-[(2,5-Diamino-6-chloro-4-pyrimidinyl)amino]-2-cyclopentene-1-methanol (VIIIa, 35 mg, 16%) eluted with 5% methanol-ethyl acetate. Continued elution with 10% methanol-ethyl acetate gave (1S,4R)-4-[2-amino-6-(cyclopropylamino)-9H-purin-9-yl]-2-cyclopentene-1-methanol(IXa) as a light tan solid foam (160 mg, 60%); N-NMR (DMSO-d6)δ: 7.58 (s, 1, purine CH), 7.25 (d, J=4.5 Hz, NH), 6.10 (m, 1, =CH), 5.80–5.75 (m, 3, =CH and NH2), 5.40 (m, 1, NCH), 4.72 (m, 1, OH), 3.45 (m, 2, OCH2), 3.0 (br m, 1, CH of cyclopropyl), 2.80 (br m, 1, CH), 2.70–2.50 (m overlapping solvent, CH), 1.50–1.05 (m,1, CH), 0.70–0.50 (m, 4, 2 CH2 of cyclopropyl).

Anal. Calcd. for $C_{14}H_{18}N_6O.0.20 H_2O.0.40 CH_3OH$: C, 57.32; H, 6.35; N, 27.85. Found: C, 57.59; H, 6.48; N, 27.70.

EXAMPLE 10

(1S,4R)-4-[2-Amino-6-(cyclopropylamino)-9H-purin-9-yl]-2-cyclopentene-1-methanol (IXa)

(1S,4R)-4-(2-Amino-6-chloro-9-H-purin-9-yl)-2-cyclopentene-1-methanol (U.S. Pat. No. 5,206,435) or the hydrochloride salt thereof (Example 8) was refluxed in ethanol with 10 molar equivalents of cyclopropylamine for 2 hours. The resulting solution was cooled to ambient temperature and 1 N sodium hydroxide (1 or 2 molar equivalents, depending on whether the starting material was VIIa or the hydrochloride salt of VIIa) was added. The volatiles were evaporated in vacuo. (1S,4R)-4-[2-Amino-6-(cyclopropylamino)-9H-purin-9-yl]-2-cyclopentene-1-methanol (IXa) was washed from a silica gel pad eluted with 5% methanol-chloroform or 10% methanol-ethyl acetate and isolated as a white solid foam (80%); spectra identical to those of the product of Example 9.

EXAMPLE 11

(1'S,3'S,4'S)-2-Amino-1,9-dihydro-9(3,4-dihydroxy-3-hydroxymethyl-1-cyclopentyl)-6H-purin-6-one
a) (4R)-4-[(2-Amino-6-chloro-5-formamido-4-pyrimidinyl)amino]-1-cyclopentene-1-methanol By the method of Example 7, N-(2-Amino-4,6-dichloro-5-pyrimidinyl)formamide (Example 3, 2.56 g, 52.4 mmol) was reacted with (4R)-4-amino-1-cyclopentene-1-methanol (1.4 g, 52.4 mmol), available from (−)-2-azabicyclo[2.2.1]hept-5-en-3-one (Chiroscience) by methods described in Examples 1–4 and 42 of U.S. Pat. No. 5,049,671. Crystallization from ethyl acetate-methanol gave title compound as white crystals, m.p. 148–150° C.; mass spectrum (CI/CH$_4$): 286, 284 (M+1), 190, 188 (B+H); $^1$H-NMR (DMSO-d$_6$)δ:

8.97 and 8.55 (s and d with J=11.3 Hz, total 1, NHCHO), 8.12 and 7.80 (s and d with J=11.5 Hz, total 1, CHO), 7.00 and 7.78 (both d, J=7.4 Hz, total 1, NH), 6.60 and 6.40 (both 8, total 2, $NH_2$), 5.48 (s, 1, =CH), 4.74 (t, J=5.5 Hz, 1, OH), 4.74–4.60 (m, 1, NCH), 4.0–3.90 (m, 2, $CH_2O$), 2.75–2.55 and 2.40–2.15 (both m, 2 each, $2CH_2$); $[\alpha]589^{20}$–4.4°, $[\alpha]578^{20}$–5.2°, $[\alpha]546^{20}$–4.8°, $[\alpha]436^{20}$–20.0°, $[\alpha]365^{20}$–60.4° (c 0.25, methanol).

Anal. Calcd. for $C_{11}H_{14}N_5O_2Cl$: C, 46.57; H, 4.97; N, 24.69; Cl, 12.50. Found: C, 46.64; H, 5.01; N, 24.60; Cl, 12.45.

b) (4R)-4-(2-Amino-6-chloro-9H-purin-9-yl)-1-cyclopentene-1-methanol

A mixture of (4R)-4-[(2-amino-6-chloro-6-formamido-4-pyrimidinyl)amino]-1-cyclopentene-1-methanol (Part a, 1.60 g, 5.65 mmol) and triethylorthoformate (29 mL) was stirred while concentrated hydrochloric acid (37%, 2.0 mL) was added in one portion. The resulting clear, colourless solution was stirred under nitrogen. After 5 hours the resulting precipitate was filtered and washed with t-butyl methyl ether (3×10 mL0 and dried to provide white powder (1.25 g). This powder was dissolved in water and the pH adjusted to 3 by addition of 1N hydrochloric acid. The solution was heated at 60° C. for 4 hours, cooled, neutralized, and evaporated to a solid which was chromatographed on silica gel. Title compound was eluted with 5% methanol chloroform and crystallized from ethanol-ethyl acetate to white crystals, m.p. 145–147° C.; mass spectrum (Cl/$CH_4$): 268, 266 (M+1), 172, 170 (B+H); $^1$H-NMR (DMSO-$d_6$)δ: 8.09 (s, 1, purine CH), 6.9 (br s, 2, $NH_2$), 5.64 (m, 1, =CH), 5.2–5.0 (m, 1, NCH), 4.87 (t, J=5.5 Hz, 1, OH), 4.05 (m, 2, $CH_2O$), 3.0–2.5 (m, 4, 2 CH2).

Anal. Calcd. for $C_{11}H_{12}N_5OCl$: C, 49.06; H, 4.64; N, 26.01; Cl, 13.16. Found: C, 49.18; H, 4.63; N, 26.11; Cl, 13.19.

c) (1S,2S,4R)-4-(2-Amino-6-chloro-9H-purin-9-yl)-2-(hydroxymethyl)-1,2-cyclopentanediol (4R)-4-(2-Amino-6-chloro-9H-purin-9-yl)-1-cyclopentene-1-methanol (Part b, 501 mg, 1.89 mmol), N-methylmorpholine N-oxide (60% aqueous solution, Aldrich, 0.33 mL, 1.89 mmol), osmium tetroxide (2.5% in t-butyl alcohol, Aldrich, 0.47 mL), and t-butyl alcohol (12 mL) were heated at 60° C. for 1.5 hours. Volatiles were evaporated and the residual solids were chromatographed on silica gel. Title compound was eluted with 10% methanol-chloroform as tan solid (210 mg) and resolidified from absolute ethanol to give white powder, m.p. 217–219° C.; mass spectrum (Cl/$CH_4$): 302, 300 (M+1), 172, 170 (B+H); $^1$H-NMR (DMSO-$d_6$)δ: 8.29 (s, 1, purine CH), 6.9 (br s, 2, $NH_2$), 5.15–4.90 (m, 1, NCH), 4.80 (d, J=3.9 Hz) overlapping 4.78 (t, J=3.5 Hz, total 2, 2 OH), 4.30 (s) overlapping 4.3–4.2 (m, total 2, OH and OCH), 3.45–3.35 (m, overlapping water, $CH_2OH$), 2.25–2.05 (m, 4, 2 $CH_2$).

Anal. Calcd. for $C_{11}H_{14}N_5O_3Cl$: C, 44.08; H, 4.71; N, 23.37; Cl, 11.83. Found: C, 43.89; H, 4.80; N, 23.16; Cl, 11.73.

d) (1'S,3'S,4'S)-2-Amino-1,9-dihydro-9-(3,4-dihydroxy-3-hydroxymethyl-1-cyclopentyl)-6H-purin-6-one (1S,2S,4R)-4-(2-Amino-6-chloro-9H-purin-9-yl)-2-(hydroxymethyl)-1,2-cyclopentanediol (Part c, 90 mg, 0.27 mmole) was refluxed in 1N hydrochloric acid (2.7 mL) for 45 minutes. Volatiles were evaporated in vacuo. Portions of water were evaporated and the residue was redissolved in water. The pH was adjusted to 5 with hydrochloric acid and the resulting mixture cooled, filtered, and the precipitate dried to provide the title compound as an off-white powder (51 mg, 68%), m.p.>300° dec.; mass spectrum (CI/$CH_4$): 283 (M+1); $^1$H-NMR (DMSO-d6) identical with that described in U.S. Pat. No. 5,233,041.

EXAMPLE 12

N-(2,4-Diamino-6-chloro-5-pyrimidinyl)formamide

N-(2-Amino-4,6-dichloro-5-pyrimidinyl)formamide (Example 3, 500 mg, 2.14 mmol) and ammonia (150 mL) was stirred in a Parr bomb at 50° C. for 18 hours. The ammonia was evaporated and the residual solid triturated with water (10 mL). The solid was dried to give the title compound as red powder (400 mg, 89%), m.p.>300° C.; mass spectrum (CI/$CH_4$): 190, 188 (M+1); $^1$H-NMR (DMSO-$d_6$)δ: 9.05 and 8.60 (both br s, total 1, NHCHO), 8.1 and 7.8 (both br s, total 1, NHCHO), 6.80–6.20 (4 br s, total 4, 2 $NH_2$).

Anal. Calcd. for $C_5H_6N_6OCl$: C, 32.01; H, 3.22; N, 37.34; Cl, 18.90. Found: C, 31.97; H, 3.23; N, 37.26; Cl, 19.00.

What is claimed is:

1. A compound of formula (III)

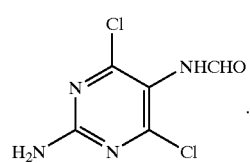

(III)

* * * * *